United States Patent [19]

Grizel et al.

[11] Patent Number: 5,601,987
[45] Date of Patent: Feb. 11, 1997

[54] IMMUNODIAGNOSIS OF PARASITOSES DUE TO A PROTOZOON IN MOLLUSKS

[75] Inventors: Henri Grizel, Arvert; Eric Mialhe, La Tremblade; Francis Paolucci; Hervé Rogier, both of Montpellier, all of France

[73] Assignees: Sanofi; Institut Francais de Recherche pour L'Exploitation de la mer - Ifermer, both of Paris, France

[21] Appl. No.: 185,439

[22] Filed: Apr. 25, 1988

[30] Foreign Application Priority Data

Apr. 24, 1987 [FR] France ................................. 87 05856

[51] Int. Cl.⁶ ..................... G01N 33/569; G01N 33/577
[52] U.S. Cl. ................. 435/7.22; 435/70.21; 435/172.2; 435/947; 435/961; 435/975; 436/518; 436/536; 436/548; 530/388.6; 530/391.1; 530/391.3
[58] Field of Search ......................... 435/7, 70.21, 172.2, 435/240.27, 947, 810, 7.22, 975, 961; 436/518, 536, 548; 530/387, 386, 391.1, 391.3

[56] References Cited

FOREIGN PATENT DOCUMENTS

A-2543970  4/1948  France .
2138445    10/1984 United Kingdom .
PCTUS8201100 8/1981 WIPO .

OTHER PUBLICATIONS

Michelson, "Application of Biotechnology to the Study of Molluscan Hosts of Animal Parasites", Southeast Asian J. Trop. Med. Pub. Hlth., 19, (1), Mar. 1988, 47–53.
Musial et al, "Detection of Cryptosporidium in Water by Using Polypropylene Cartridge Filters", Applied and Environmetal Microbiology, 53 (4) Apr. 1987, 687–692.
Elston et al, "Occurence and Significance of Bonamiasis in European Flat Oysters *Ostrea edulis* in North America", Dis. Aquat. Org., 2 (1), 1986, 49–54.
Biological Abstracts, vol. 83, 1987, No. 95635.
Biological Abstracts, vol. 77, 1984, No. 76034.
Biological Abstracts, vol. 84, 1987, No. 96907.

*Primary Examiner*—David Saunders
*Attorney, Agent, or Firm*—Bacon & Thomas

[57] ABSTRACT

This invention relates to a monoclonal antibody which specifically recognises an antigen of a protozoon parasitizing a mollusk.

Application: immunodiagnosis of parasitoses due to a protozoon in mollusks.

9 Claims, No Drawings

IMMUNODIAGNOSIS OF PARASITOSES DUE TO A PROTOZOON IN MOLLUSKS

BACKGROUND OF THE INVENTION

1. Field of the Invention

The present invention relates to monoclonal antibodies directed specifically against an antigen of a protozoan parasitizing a mollusk. It relates more particularly among these monoclonal antibodies to those which are directed against an antigen of a protozoon belonging to the phylum of Ascetospora as defined by LEVINE N. D. et al.((1980) A newly revised classification of the Protozoa., 27, 37–58). And among these antibodies it relates more especially to those which are directed against an antigen of the protozoon *Bonamia ostreae,* parasite of the flat oyster species *Ostrea edulis* L.

2. Brief Review of the Prior Art

It is known that mollusks, particularly sea mollusks, can be parasitized by a protozoon. Several pathogenic protozoa have been identified, particularly among the genera Minchinia, Haplosporidium and Marteilia (GRIZEL H. et al. (1974) Science et Pêches, Bull. Inst. Pêches Marit., No. 240, 7–30; PERKINS F.O. (1979) Mar. Fish Rev., 41 (1–2), 25–37). Another protozoon, *Bonamia ostreae,* which is the cause of a parasitosis of flat oyster cultivation beds in France has, since it was brought to light (COMPS M. et al. (1980) C. R. Acad. Sc. Paris, 290, ser. D, 383–384), been the subject of numerous studies focusing both on its structure (PICHOT Y. et al. (1980) Rev. Trav. Inst. Pêches Marit., 43 (1), 131–140) and on the epidemiologic situation resulting from its presence (TIGE G. et al. (1981) Science et Pêche, Bull. Inst. Pêches Marit., No. 315, 13–20).

These parasitoses decimate the mollusk populations. They can lead to the disappearance of species. They have, of course, an impact of considerable economic importance when they affect cultivated mollusks (GRIZEL H. (1983) Cons. Int. ExpLor. Met, Gert.: 9, 30 p), especially when they take the form of an endemic epizootic. This is precisely the case in the parasitosis of the oyster *Ostrea edulis* L. in which the etiologic agent is *Bonamia ostreae,* in respect of which it has been experimentally observed that a single individual was able to cause the death of an oyster to which it had been inoculated four months earlier. This parasitosis, having been identified successively in various French oyster beds, is now found in certain oyster-farming basins in several European states, particularly Spain, Ireland, the Netherlands and the United Kingdom, and in the United States of America; it may also be noted that at present a protozoon of the genus Bonamia is suspected of being at the origin of a parasitosis of the flat oyster species *Ostrea luteria* in New Zealand.

The importance of the economic stakes associated with these parasitoses has led to a search for measures making it possible, if not to eradicate them, at least to check them.

These measures are most often of a prophylactic nature when no breed of the mollusk concerned has been found which is resistant to the parasitosis or when no anti-parasitic treatment has proven efficacious. They then consist essentially in preventing the introduction, into healthy cultivation beds, of animals which are already parasitized. They thus require, for their implementation, the availability of an effective method of diagnosis characterized by its ease of use and its reliability.

No such method of diagnosis has been described. In fact, the only known method consists in carrying out histological examinations on the mollusks. This method is poorly suited for a routine practice because of the means required for its implementation and the necessary recourse to a specialist for interpretation of the results. Moreover, strictly speaking it does not permit quantification of the degree of infestation of the parasitized mollusks. Another important disadvantage is the length of time between the preparation of the samples and the availability of the results.

The Applicant has now found a method which is simple to use and reliable and is based on the use of monoclonal antibodies. Given that the mollusks, faced with a parasitic infestation, are unable to develop a humorally-mediated immune response of the antibody type, it appeared in fact to the applicant that it was necessary to demonstrate the presence of the protozoa themselves. Now, a mono-clonal antibody specifically recognising an antigen of a protozoon constitutes a sure means for demonstrating its presence.

The obtaining of monoclonal antibodies recognising an antigen of a protozoon has already been described within the scope of studies focusing on protozoa of the genus Leishmania which, as parasites of human white corpuscles, are, from a phylogenetic point of view, substantially distant from the protozoa parasitizing the mollusks. But the available publications (particularly the international patent application WO 86/02098) do not allow the particular difficulties to be overcome which, associated with the isolation and the purification of a protozoon from mollusks which it has parasitized, did not exist in the case of the protozoa of the genus Leishmania which it is possible to cultivate and for which there exist pure strains in various collections.

SUMMARY OF THE INVENTION

The Applicant has in fact developed a method for obtaining monoclonal antibodies recognising an antigen of a protozoon parasitizing a mollusk, by conceiving a method for the purification of the said protozoon, permitting the preparation of a purified and concentrated suspension which is essential for appropriate immunization of laboratory animals.

For the implementation of the invention according to its various aspects the term mollusk should be understood as any animal belonging to the phylum of mollusks which itself comprises three main classes: The gastropods, the lamellibranches and the cephalopods. The invention can relate to any mollusk, whatever the influence of man on its environment: it may or may not be a cultivated mollusk. It is sufficient that the said mollusk is parasitized by a protozoon. The invention is particularly suitable for obtaining monoclonal antibodies for detecting and measuring their degree of infestation by protozoa belonging to the phylum of Ascetospora and, particularly among these protozoa, by those which, such as *Bonamia ostreae,* have as their target the blood cells of the mollusk.

According to a first aspect, the invention relates to any monoclonal antibody specifically recognising an antigen of a protozoon parasitizing a mollusk.

It relates more particularly to any monoclonal antibody specifically recognising an antigen of *Bonamia ostreae*. In a preferred manner it relates to the monoclonal antibody secreted by the hybridoma of which a sample of a culture was deposited at the European Collection of Animal Cell Cultures (ECACC, United Kingdom) on 23 Apr. 1987 and to which the said collection allocated the reference 87042307. This antibody, hereinafter designated by reference 20B2-1B12, belongs to the IgG2a class and has an isoelectric point of 6.9 to 7.3. It has, relative to nine other monoclonal antibodies selected and produced by the Applicant, other characteristics which will be presented hereinafter in Example 4.

According to another aspect, the invention relates to method for obtaining the said monoclonal antibodies. This method comprises the following successive steps:

a) preparation, from parasitized mollusks, of a purified suspension of the protozoon, b) immunization of laboratory animals by means of the said suspension, c) lymphocyte hybridization between the splenic lymphocytes of an animal and the myelomatous cells, d) selection of the hybridomas secreting a monoclonal antibody specifically recognising an antigen of the said protozoon; and e) cloning of the hybridomas and production of the antibodies.

The preparation of a purified suspension of the protozoon involves an operation for crushing the body of the mollusks, which is carried out in such a way that the mollusk cells containing the protozoa rupture and the protozoa are collected intact after several centrifugation operations permitting progressively the elimination of the mollusk cells and the cellular debris of all kinds contained initially in the crushed mixture.

In order to collect the largest possible number of protozoa, it is advantageous to subject the entire body of the mollusks to crushing; this operating method takes advantage of the dominant role which the blood cells of a mollusk can play in its infestation, which cells, because the circulatory system of mollusks is not closed, are found dispersed in all the tissues. However, it is convenient to remove be forehand any organ of a fibrous nature such as, in the mollusks of the lamellibranch class, the adductor muscle of the bivalve shell. Indeed, an organ of this kind would lead to the formation of aggregates and would be an obstacle to appropriate homogenization of the crushed mixture.

Obtaining a crushed mixture in which the protozoa are preserved involves using a liquid, described hereinafter as homogenization liquid, maintaining a protective environment around the protozoa. This liquid must be added as early as the crushing phase. In an advantageous manner, sea water is used which is deprived of contaminant microorganisms, particularly bacteria, and whose osmotic pressure has been adjusted—if it had a lower value—to about 1,000 mosm by means of sodium chloride, and a surfactant is added. In a preferred manner, a neutral surfactant is used. Polyoxyethylene sorbitan 20 monooleate of the type marketed under the name Tween® 80 is particularly well suited. The surfactant is added to the sea water at a ratio of 0.5 to 2% (v/v) and, in a preferred manner, at a ratio of 1% (v/v).

An apparatus which is particularly well suited for crushing the mollusks is that marketed under the name Ultra-Turrax by the company IKA JAUKE und KUNKEL (Federal Republic of Germany). Among the generating shafts with which this device can be equipped, that bearing reference No. 18K is preferred.

The crushing is advantageously carried out in two steps: a homogenization following a first phase of laceration of the body of the mollusks.

The homogenized crushed mixture is then subjected to a treatment of clarification and concentration of the particulate elements. This treatment advantageously comprises a filtration followed by a centrifugation of the resulting suspension. The filtration is intended to allow the removal of the largest particulate elements. The centrifugation is intended to allow the removal of the solution and the concentration of the particulate elements remaining, by recovering the centrifugation residue by means of homogenization liquid at a volume less than the initial volume.

For example, the filtration is carried out successively on three nylon cloths of meshes equal to 300, 60 and then 25 μm, and the centrifugation of the filtrate is carried out at 2,000 g for 30 minutes.

This first treatment resulting in obtaining an homogenized and filtered crushed mixture should be followed by a treatment for removal of the particulate elements other than the protozoa sought. This further treatment advantageously comprises several differential centrifugations, for example on sucrose, with or without a gradient, succeeding each other in such a way as to remove progressively, depending on their size and their density, the particulate elements which are undesired.

A final centrifugation of an isopycnic nature makes it possible, if necessary, to attain a high degree of purification. All these purifications are carried out according to the techniques known to the person skilled in the art. It is possible eventually to collect up to $10^6$ to $10^7$ protozoa from a parasitized mollusk.

The purified suspension of protozoa obtained is used to immunize laboratory animals. Mice may be conveniently used. The scheme and the protocol for immunization are established taking into consideration the quantity of protozoa collected and according to the criteria normally used by the person skilled in the art.

The lymphocyte hybridization is carried out using the lymphocytes of the spleen of an immunized mouse and myelomatous cells according to the basic technique described by KOHLER G. and MILSTEIN C. ((1975) Nature, 256, 495–497).

The selection of the hybridomas secreting a monoclonal antibody specifically recognising an antigen of the protozoon concerned requires the detection of the antibodies secreted by each hybridoma, for example by means of a radioimmunologic assay. The cells are then cloned, for example according to the technique of limited dilution. The antibody activity of each clone is measured. The expert is in a position to make a choice, from among the know techniques, of one which is suited to each particular case.

The selected hybridomas can then be frozen in liquid nitrogen. Once returned to culture on culture plates, they secrete the antibody which it is possible to identify in the culture supernatants. It is also possible to prepare the antibodies from an ascites liquid when it is desired to obtain a high concentration of antibodies. These different methods of production are well known to the person skilled in the art.

The monoclonal antibodies collected can of course then be purified, depending on the use for which they are intended, by using a known technique. A technique may advantageously be chosen for a use of the monoclonal antibodies according to the invention with a view to in vitro diagnosis of parasitoses. It consists in subjecting the preparation of monoclonal antibodies to an affinity chromatography by using a column of insolubilized protein A.

The monoclonal antibodies according to the invention constitute diagnostic tools which are of great interest due to the high specificity which characterizes the connection which can be established between an antibody an an antigen. They may be used according to various techniques known per se by the person skilled in the art. Preferably used in purified form, they can be immobilized by adsorption on an insoluble support such as, for example, a microtitration plate. They can also be coupled to a marker. All kinds of known markers are suitable: These may be in particular a fluorescent marker, a radioactive isotope or even an enzyme. In an advantageous manner the monoclonal antibodies according to the invention, for example adsorbed onto a solid support or with a maker, and made available to the users, constitute one of the components of a diagnostic kit comprising the essential elements for carrying out the detection or determination envisaged.

According to another aspect, the invention relates precisely to the use of the said monoclonal antibodies as in vitro diagnostic tools for parasitoses affecting mollusks, in which the etiologic agent is a protozoon. These monoclonal antibodies make it possible, for each animal tested, to detect the parasitic protozoa and, by a determination, to measure their degree of infestation. It thus also relates to a diagnosis kit comprising a sample of at least one preparation based on a monoclonal antibody according to the invention.

The invention thus provides a reliable solution to the important problem posed by the monitoring of the state of health of the mollusks, which alone permits the establishment up of a strategy for zoosanitary prophylaxis.

According to another aspect, the invention relates to the hybridomas secreting a monoclonal antibody specifically recognising an antigen of a protozoon parasitizing a mollusk. The preferred hybridoma is the one deposited at the ECACC under reference 87042307.

In the following, embodiment examples and use examples of the various aspects of the invention are shown. Although they relate to monoclonal antibodies directed against the protozoon *Bonamia ostreae,* it should be understood that the invention is not limited to these antibodies alone and in particular to their production and their use, but relates in a general manner to the monoclonal antibodies recognising an antigen of a protozoon parasitizing a mollusk and, more particularly, those recognising an antigen of a protozoon belonging to the phylum of Ascetospora.

Various buffers, mentioned hereinafter in the examples, will be referred to for convenience by an abbreviation. These buffers are:

PBS: $KH_2PO_4$ 10 mmol/l, NaCl 150 mmol/l, pH set at 7.4

PBS1: PBS buffer to which there is added, at a ratio of 0.1 % (w/v), bovine serum albumin marketed by the company SIGMA under the reference A 4503.

PBS2: PBS buffer to which there is added, at a ratio of 0.5% (w/v), bovine serum albumin (SIGMA).

PBS3:PBS2 buffer to which there is added, at a ratio of 0.5% (v/v), polyoxyethylene sorbitan 20 monolaurate marketed by the company MERCK (USA) under the reference 822 184 and under the name Tween® 20, hereinafter designated polysorbate 20.

PBS4: PBS buffer to which there is added, at a ratio of 2% (w/v), bovine serum albumin (SIGMA).

PBS5:PBS4 buffer to which there is added, at a ratio of 0.75% (w/v), glycine marketed by the company MERCK (USA) under the reference 4201.

PSB6: PBS buffer to which there is added, at a ratio of 0.5 (v/v), glutaraldehyde marketed by the company SIGMA under the reference G 6257.

IF: Buffer for immunofluorescence marketed by the company Diagnostics Pasteur (FRANCE) under the reference 74903.

IF-EVANS: IF buffer to which there is added, at a ratio of 1/10,000 (v/v), EVANS blue TBS: Tri(hydroxymethyl)aminomethane: 10 mmol/l, NaCl 100 mmol/l, pH set at 7.4.

TBS1: TBS buffer to which there is added, at a ratio of 1% (v/v), polysorbate 20.

TBS2: TBS buffer to which there is added, at a ratio of 0.1% (v/v), polysorbate 20.

Microtitration plates are used. These are polystyrene plates marketed by the company NUNC (USA) under the reference 2-69620.

The culture plates used are those marketed by the company FALCON (USA) under the reference 3072.

Nitrocellulose filters 6 mm in diameter are placed in the wells of the microtitration plates. They are cut out, using a hollow punch, from nitrocellulose filters marketed by the company SCHLEICHER and SCHULL (FRG) under references BA 83/No. 401380.

EXAMPLE

1. PREPARATION OF A SUSPENSION OF *Bonamia ostreae* a) Crushing 10 oysters from an oyster bed from the basin of the bay of Quiberon (Morbihan—FRANCE) and infected by *Bonamia ostreae* are prepared.

The shells are removed from the bodies and the adductor muscle is cut off and discarded.

The 10 bodies thus prepared are introduced into a beaker with a capacity of 500 ml and whose section has a diameter of 10 cm. 300 ml of sea water whose osmotic pressure has been adjusted to 1,000 mosm are added, filtered through a membrane having pores of a maximum diameter of 0.22 μm, and polyoxyethylene sorbitan 20 monooleate marketed by the company SIGMA (USA) under the name Tween®80 and under the reference P 1754 is added at a ratio of 1% (v/v). In the text which follows this homogenization liquid is hereinafter referred to, for convenience sake, by the abbreviation S.W.F.T.

The generating shaft No. 18K mounted on an ULTRA-TURRAX device is introduced into the beaker and then set in rotation at about 8,000 rpm. When there is no longer any observable tissue material, the rotation is stopped and the generating shaft is removed from the beaker.

The crushed mixture obtained is transferred into series of Thomas Potter tubes whose diameter at the level of the tube proper is slightly greater than that (25 mm) of the generating shaft.

The generating shaft rotating at 8,000 rpm is plunged ten times one after the other into the crushed mixture in one of the tubes. The same operation is repeated on each of these tubes. The contents of the various tubes are brought together. They constitute a homogenized crushed mixture which is filtered successively on three nylon cloths of meshes equal to 300, 60 and then 25 μm.

This homogenized and filtered crushed mixture contains intact oyster cells, debris from such cells, particularly the nuclei, some of the contaminating organisms, and the protozoa sought.

b) Centrifugations

The crushed mixture obtained at a) is divided among 10 tubes. Each tube is subjected to a centrifugation at 2,000 g for 30 minutes at 8° C. The residue R1 obtained is suspended again by ULTRA-TURRAX homogenization in 10 ml of S.W.F.T. (suspension S1).

Each suspension S1 is then subjected to a differential centrifugation. 10 ml of the suspension S1 are deposited on the surface of 30 ml of a 20% (w/w) solution of sucrose in S.W.F.T.; after centrifugation at 2,000 g for 30 minutes at 8° C., the residue R2 obtained is suspended again in 5 ml of S.W.F.T. (suspension S2). This differential centrifugation has permitted the elimination of debris of small dimension and of contaminating microorganisms. Each suspension. S2, at a volume of 5 ml, is deposited on a discontinuous density gradient of sucrose prepared from 15 ml of a 20% (w/w) solution of sucrose in S.W.F.T. and 30 ml of a 40% (w/w) solution of sucrose in S.W.F.T. After a centrifugation at 2,000 g for 30 minutes at 8° C, it is observed that the protozoa sought are distributed up at the interface of the two solutions. The larger or denser cellular debris have penetrated into the fraction corresponding to a 40% concentration of sucrose. The fractions corresponding to the interface are collected and combined.

The suspensions thus obtained of the desired protozoa from the 10 S2 suspensions are grouped together, diluted with an equal volume of S.W.F.T., and distributed into 3 tubes for centrifugation at 2,000 g for 30 minutes at 8° C. The 3 residues R3 are taken up again in S.W.F.T. The suspension S3 obtained contains, at a volume of 5 ml, all the desired protozoa from the 10 oysters treated.

This suspension can be used as it is. Continuing the purification with an isopycnic centrifugation makes it possible to obtain results of an increased quality. This last purification step is carried out by subjecting the suspension S3, divided beforehand among 10 tubes, is deposited on a double discontinuous gradient of density and tonicity of a silica polydisperse colloid covered with polyvinylpyrrolidone marketed under the name PERCOLL® by the company PHARMACIA (Sweden). Beginning with a stock solution of PERCOLL whose osmotic pressure has been adjusted beforehand to 1,400 mosm by means of NaCl added until the NaCl concentration reaches 0.7 mol/l, five solutions of PERCOLL, at 30%, 40%, 50%, 60% and 70% (v/v) in S.W.F.T., are prepared. The osmotic pressure gradient thus created is of between 1,100 mosm (corresponding to a 30% concentration of PERCOLL) and 1,300 mosm (corresponding to a 70% concentration of PERCOLL). After centrifugation at 2,000 g for 30 minutes at 8° C., the desired protozoa concentrate principally at the 60–70% interface. The fractions corresponding to this interface are colletted and constitute the SP1 suspension. The 50–60% interface also contains protozoa, but these are in a smaller amount and are combined with some debris.

The SP1 suspension contains only protozoa, to which, nevertheless, membrane fragments from the parasitophoric vacuole of the oyster cell may remain attached. Ultrastructural examinations and experimental infections have confirmed that their structure has not been altered.

The pool of the 10 SP1 suspensions from the treatment of the 10 parasitized oysters, collected in a volume of 6 ml, contains about $5/10^7$ protozoa. This pool may be used as it is, However, for an application such as the adsorption of the protozoa on the surface of a microtitration plate, it is necessary to remove the PERCOLL from it, This can be achieved by centrifuging, at 2,000 g for 30 minutes at 8° C., 12 mL of the suspension obtained by dilution volume by volume of suspension SP1 in S.W.F.T., placed on a cushion of 2 ml of a 20% (w/w) solution of sucrose in S.W.F.T. The residue taken up again in 20 ml of S.W.F.T. constitutes the suspension SP2 which is deprived of PERCOLL and contains about $2.5 \times 10^6$ protozoa per ml.

2. PREPARATION OF A PURIFIED SUSPENSION OF *HAPLOSPORIDIUM ARMORICANUM*

A purified suspension of spores of *Haplosporidium armoricanum* was obtained by subjecting parasitized oysters of the *Ostrea edulis* L. species, taken from a natural bed of the Thau region (Herault—FRANCE), to the protocol used in Example 1. These spores have a slightly greater density than that of the cells of *Bonamia ostreae* and concentrate, on isopycnic centrifugation, not at the 60–70% interface but at the bottom of the 70% fraction.

3. OBTAINING ANTI-*BONAMIA OSTREAE* MONOCLONAL ANTIBODIES 3.1. Lymphocyte hybridization a) Immunization of laboratory mice 6 female mice of the Balb/c breed each receive, at zero time, 800 µl of the SP1 suspension obtained in Example 1 diluted 1:1 in Freund's adjuvant, at a rate of 500 µl intraperitoneally, 200 µl intravenously and 100 µl intramuscularly. Each mouse is then subjected to seven boosters, each one carried out following this protocol. The first of these boosters is effected one month after the initial series of injections, and the subsequent six boosters follow each other at monthly intervals. The seventh booster is followed one month later by a final booster effected in the presence of promethazine (Sigma—reference p 4651). The mice are sacrificed three days after the final booster.

b) Fusion $300 \times 10^6$ B lymphocytes collected from the spleen of an immunized mouse are placed in contact with $150 \times 10^6$ cells of the myelomatous line P3×63 Ag 8–653, in the presence of polyethylene glycol marketed under the reference PEG 1540 by the company RIEDEL-DE-HAEN (FRG). The fusion is carried out according to the technique described by J. GODING ((1980) J. Immunol. Methods, 39, 285).

The cellular suspension is distributed, at a ratio of $10^5$ cells per well, in the wells of culture plates each containing $10^4$ peritoneal macrophages of mice. HAT medium containing, in a mixture, hypoxanthine, aminopterin and thymidine is added 25 h after the fusion.

3.2. Selection of the hybridomas secreting a monoclonal antibody specifically recognising an antigen of *Bonamia ostreae*

An operating procedure is used which is based on the detection, by an indirect radioimmunologic method, of an antibody activity of the culture supernatants from the wells of culture plates relative to, on the one hand, a purified suspension of *Bonamia ostreae,* and, on the other hand, a crushed mixture prepared from a flat oyster of the *Ostrea edulis* L. species free from *Bonamia ostreae*.

Preparation of microtitration plates a) Plates bearing protozoa adsorbed at the surface Each well receives 50 µl of a solution of poly-L-lysine at 20 µg/l in PBS buffer. After contact for 30 minutes at 20° C., the plates are emptied by inversion and each well receives 100 µl of the SP2 suspension of *Bonamia ostreae* obtained in Example 1, i.e. about 250,000 protozoa. The plates are centrifuged at 2,000 g for 30 minutes at 8° C. Then 20 µl of PBS6 buffer are poured into each well. The plates are then incubated for 8 minutes at 20° C. and washed twice with the PBS buffer. The wells are then saturated with 200 µl of PBS5 buffer. After contact for 30 minutes at 20° C., the wells are washed with the PBS buffer. Finally, the wells having received 100 µl of PBS4 buffer, the plates are frozen at –20° C.

b) Control plates

They are prepared as indicated above, but the SP2 suspension is replaced by the crushed mixture of an oyster free from *Bonamia ostreae*. Non-parasitized oysters originating from the Belle-Isle bed (Morbihan FRANCE) and free from *Bonamia ostreae* were maintained in culture in the laboratory for 12 months and, at the end of this period, a histological check was carried out in order to verify the absence of *Bonamia ostreae*. For the preparation of the test crushed mixture: an oyster is crushed in 500 ml of sea water and the crushed mixture is filtered through a nylon cloth having a mesh of 25 µm.

2—Detection test

At the moment of use, the microtitration plates are thawed and washed three times with the PBS buffer. Each well receives 50 µl of one of the culture supernatants obtained in 1.2.B and 50 µl of PBS3 buffer. After an incubation of 2 hours at 37° C., the plates are washed three times with a wash solution made up of a 150 mmol/l NaCl solution to which polysorbate 20 is added at a ratio of 0.5% (v/v). An iodine-125-labeled anti-mouse immunoglobulin antibody from sheep, marketed by the company ZYMED (USA), is diluted with the PBS3 buffer in such a way as to have an activity of 300,000 cpm/100 µl. It is then divided at a ratio of 100 µl per well. After an incubation of one hour at 37° C., the plates are washed five times with the wash solution, and the radioactivity of each well is measured.

3—Results The amount of the activity of the culture supernatants measured in the wells of the microtitration plates makes it possible to identify those of the culture plate wells which contain at least one hybridoma secreting a monoclonal antibody:

specifically anti-*Bonamia ostreae* (type BO antibody activity)

or anti-oyster non-parasitized by *Bonamia ostreae* (type HS antibody activity), or anti-*Bonamia ostreae* and anti-oyster non-parasitized by *Bonamia ostreae* (type NS antibody activity).

Table 1 shows by way of example measures carried out on three culture supernatants having an antibody activity of type BO, HS or NS. The non-specific fixation of the iodine-125-labeled anti-mouse immunoglobulin antibody from sheep was measured on wells prepared as indicated above in paragraph 2, placing in these, however, not 50 µl of a culture supernatant, but 50 µl of fresh culture medium (RPMI 1640 medium marketed by the company GIBCO (USA) to which there is added at a ratio of 10% (v/v) of fetal calf serum).

TABLE 1

| | | Activity (cpm) measured in the wells of the microtitration plates | |
|---|---|---|---|
| | | Microtitration plates with protozoa adsorbed at the surface | Control microtitration plates |
| Antibody activity type of the supernatant added to the wells | BO | 2,000 | 500 |
| | HS | 100 | 10,000 |
| | NS | 4,000 | 8,000 |
| Non-specific binding | | 50 | 400 |

In the final analysis, of the 1,718 wells of culture plates tested, 703 contained at least one hybridoma coming under one of the three categories.

3.3. Cloning of the hybridomas and production of the antibodies 8 culture plate wells were cloned by the technique of limiting dilution. 10 clones of hybridomas secreting a specifically anti-*Bonamia ostreae* monoclonal antibody were selected. These clones were frozen in liquid nitrogen. The antibodies which they secrete were purified, using ascites liquid from female Balb/c mice, by affinity chromatography on a gel of Sepharose ® protein A marketed by the company PHARMACIA (Sweden) according to the technique described by EY P. L. et al. (1978) Immunochemistry, 15, 429–436).

4. CHARACTERIZATION OF THE MONOCLONAL ANTIBODIES SPECIFICALLY ANTI-*BONAMIA OSTREAE*

4.1. Immunologic characterization

1) Operating procedure

The immunologic characterization of the different epitopes recognised by 10 selected monoclonal antibodies was carried out by a competition between one of the antibodies which was labeled in the conventional manner with 125-iodine and another of these antibodies which was not labeled for their binding to the protozoa adsorbed on a nitrocellulose filter.

A nitrocellulose filter of 6 mm diameter is introduced into each of the wells of a microtitration plate. 25 µl of the SP1 suspension obtained in Example 1 or of a crushed mixture of oyster free from *Bonamia ostreae* are introduced into each well. After an incubation of 18 hours at 37° C., each well is saturated with 200 µl of a PBS2 buffer for 2 hours at 37° C. The wells are then washed three times with a 150 mmol/l NaCl solution.

The iodine-125-labeled antibody to be tested is diluted in such a way that its activity is equal to 300,000 cpm/50 µl. 50 µl of this preparation containing 100 ng per ml of antibody are placed in each well. 50 µl of a preparation is then deposited which contains 10 µg per ml of another non-labeled antibody in solution in the PBS1 buffer. After an incubation of 3 h at 37° C., the filters are washed five times with a 150 mmol/l NaCl solution.

When the epitopes recognised by each of the two antibodies are close, a disappearance of the measured radioactivity is observed corresponding to the inhibition of the binding of labeled antibody.

2) Results

The following percentages of inhibition of an iodine-125-labeled antibody by a non-labeled antibody were obtained:

|  | Ab not Labeled | | | | | | | | |
|---|---|---|---|---|---|---|---|---|---|
| Ab | 2E3 | 10F1 10G9 | 15C2 | 16G5 | 16G5 | 16F11 | 16F11 | 20B2 | 20B2 |
| Labeled | 1F2 | 2D4 2D2 | 2F2 | 2E7 | 3D10 | 2A7 | 2F10 | 1B12 | 3A8 |
| 2E3-1F2 | — | — — | — | — | — | — | — | — | — |
| 10F1-2D4 | 18 | 63 21 | 10 | 39 | 39 | 6 | 17 | 0 | ND |
| 10G9-2D2 | — | — — | — | — | — | — | — | — | — |
| 15C2-2F2 | 12 | 5 0 | 80 | 12 | 8 | 0 | 9 | 0 | ND |
| 16G5-2E7 | 20 | 7 4 | 20 | 81 | 64 | 13 | 20 | 1 | ND |
| 16G5-3D10 | 9 | 3 0 | 16 | 80 | 66 | 14 | 7 | 5 | ND |
| 16F11-2A7 | — | — — | — | — | — | — | — | — | — |
| 16F11-2F10 | — | — — | — | — | — | — | — | — | — |
| 20B2-1B12 | 9 | 3 0 | 5 | 5 | 3 | 5 | 1 | 81 | 81 |
| 20B2-3AB | ND | ND ND | ND | ND | ND | ND | ND | 89 | 88 |

ND: not determined
—: antibody not immunologically active

These results make it possible to determine the existence of at least four independent epitopes on *Bonamia ostreae*.

These epitopes are recognised specifically by the selected antibodies as follows:

| EPITOPE | ANTIBODY |
|---|---|
| I | 20B2–1B12 and 20B2–3A8 |
| II | 15C2–2F2 |
| III | 16G5–2E7 and 16G5–3D10 |
| IV | 10F1–2D4 |

Epitope IV is partly covered by epitope III.

4.2 Determination of classes and subclasses

It was possible to determine the classes to which the eleven antibodies produced belong. They belong to the IgG class and, more precisely, five of them belong to the IgG1 subclasses, four others to the IgG2a subclass, and one other to the IgG3 subclass.

| ANTIBODY | SUBCLASS |
|---|---|
| 2E3–1F2 | IgG1 |
| 10F1–2D4 | IgG1 |
| 10G9–2D2 | IgG1 |
| 15C2–2F2 | IgG2a |
| 16G5–2E7 | IgG2a |
| 16G5–3D10 | IgG2a |
| 16F11–2A7 | IgG1 |
| 16F11–2F10 | IgG1 |
| 20B2–1B12 | IgG2a |
| 20B2–3A8 | IgG3 |

4.3. Determination of the isoelectric points

The isoelectric points of eight antibodies were determined by using the technique of isoelectric focusing.

| ANTIBODY | ISOELECTRIC POINT |
|---|---|
| ZE3-1F2 | 6.7 to 7.2 |
| 10F1-2D4 | 6.5 to 7.0 |
| 10G9-2D2 | 7.5 to 8.0 |
| 15C2-2F2 | 8.2 to 8.5 |
| 16G5-2E7 | 6.3 to 6.6 |
| 16F11-2A7 | 7.0 to 7.3 |
| 16F11-2F10 | 7.0 to 7.3 |
| 20B2-1B12 | 6.9 to 7.3 |

5. USE OF THE ANTI-*BONAMIA OSTREAE* MONOCLONAL ANTIBODIES 5.1. Preparation of the samples to be tested 1) Choice of tissue

*Bonamia ostreae* parasitizes the blood cells or hemocytes of the oyster. Since the circulatory system of this animal is not closed, the hemocytes are found distributed in all the organs.

A histologic study carried out on the different tissues (branchial, palpal, digestive and blood (hemolymph) tissues) shows that the hemolymph represents a tissue of choice because, on the one hand, it is representative of the infestation and, on the other hand, is easy to remove by direct puncture into the pericardial cavity.

2) Treatment of the hemolymph

After removal, the hemolymph is frozen. At the time when the test is carried out, it is thawed. This treatment promotes the rupture of the blood cells and the release of the protozoa which they contain, the latter thus becoming accessible in greater number to the molecules of the monoclonal antibody.

5.2. Preparation of the monoclonal antibodies

The antibodies used hereinafter were purified by affinity chromatography on insolubilized protein A. They were labeled by means of a radioactive isotope according to a conventional procedure or by an enzyme according to a protocol described hereinafter.

5.3. Tests

1) Visualization of the protozoa on a smear of oyster heart by a technique of indirect immunofluorescence The hemolymph of an oyster is placed on a glass slide by affixing the heart. This preparation is dried in air and fixed in acetone for 10 minutes. It is then covered with a preparation of the monoclonal antibody in solution, at a ratio of 50 µg per ml, in IF buffer. After 15 minutes of incubation at room temperature in a humidity chamber, the slide is washed with IF buffer, then covered with a solution of anti-mouse immunoglobulin goat serum conjugated with fluorescein isothiocyanate (marketed by the company DIAGNOS-TICS PASTEUR (FRANCE) diluted to 1/100 in IF-EVANS buffer. It is then incubated for 30 minutes at room temperature in a humidity chamber, then washed with IF buffer. A glass slide is deposited on the smear, with a glycerinated buffer marketed by the company DIAGNOSTICS PASTEUR being interposed between the slide and the cover glass. The slide is examined by means of an epifluorescent microscope using immersion oil. A positive reaction is manifested by a brilliant green fluorescence on small cells. The latter are *Bonamia ostreae* cells. Two negative controls are carried out, one using non-specific mouse immunoglobulin in the presence of parasitized oysters, and the other placing the monoclonal antibody in the presence of healthy oysters. This test was carried out using each of the 10 monoclonal antibodies obtained in Example 3. Identical results were observed.

2. Direct determination on nitrocellulose with an iodine-125-labeled antibody

This determination consists in carrying out the immunological binding of an anti-*Bonamia ostreae* antibody labeled with iodine-125 to oyster blood cells adsorbed beforehand directly onto a nitrocellulose filter.

A nitrocellulose filter of 6 mm of diameter is introduced into each of the wells of a microtitration plate. 25 µl of hemolymph removed from an oyster are placed on each filter. After an incubation of 15 hours at 37° C., each filter is saturated for 3 hours at 37° C. with 200 µl of TBS1 buffer. It is then washed three times with a 100 mmol/l NaCl solution. 100 µl of a preparation of the iodine-125-labeled 20B2-1B12 antibody are added, whose activity has been brought to 200,000 cpm/100 µl by dilution in TBS2 buffer. After an incubation of 2 hours and 30 minutes at 37° C., the filter is washed five times with a 100 mmol/l NaCl solution and the radioactivity of the filter is measured.

Under these conditions, the hemolymph of a severely parasitized oyster allows a signal of 100,000 cpm to be obtained, while the hemolymph of an oyster free from *Bonamia ostreae* allows a signal of 600 cpm to be obtained.

3. Determination of the sandwich type with radioactive labeling

This determination consists in immunologically trapping the parasites present in the oyster blood cells by an anti-*Bonamia ostreae* antibody adsorbed beforehand on a solid phase. The same iodine-125-labeled anti-*Bonamia ostreae* antibody is added in such a way that it is bound to the parasite. This determination is theoretically more specific than the direct determination, since only the parasites sandwiched between the two antibodies remain present in the wells of the microtitration plate.

a) Determination in 1 stage

100 µl of a preparation of the 20B2-1B12 antibody in solution, at a ratio of 20 µg per ml, in TBS buffer are deposited in each of the wells of a microtitration plate. After 15 hours of incubation at 4° C., washing is carried out using a 100 mmol/l NaCl solution. The wells are then saturated with 200 µl of TBS1 buffer for 60 minutes at 37° C. The plate is then washed with a 100 mmol/l NaCl solution. 10 µl of hemolymph from an oyster and 90 µl of a preparation of the iodine-125-labeled 20B2-1B12 antibody whose activity has been brought to 250,000 cpm/90 µl by dilution in the TBS2 buffer are added simultaneously into each well. The plate is centrifuged at 350 g for 15 minutes. After an incubation of 2 hours and 30 minutes at 37° C., the wells are washed five times with a 100 mmol/l NaCl solution and their radioactivity is measured after solubilization of the proteins by 100 µl of 4 mol/l NaOH and extraction with the Cell Harvester system marketed under the references 7070, 7071 and 7080 by the company SKATRON (USA).

b) Determination in 2 stages

100 µl of a preparation of the 20B2-1B12 antibody in solution, at a ratio of 20 µg per ml, in the TBS buffer are deposited in each of the wells of a microtitration plate. After 15 hours of incubation at 4° C, a washing is carried out using a 100 mmol/l NaCl solution. The wells are then saturated with 200 µl of TBS1 buffer for 1 hour at 37° C. The plate is then washed three times with a 100 mmol/l NaCl solution. 50 µl of hemolymph are deposited in each well in the presence of 50 µl of TBS2 buffer. The plates are centrifuged at 350 g for 15 minutes, then incubated for 3 hours at 37° C. The wells are then washed 3 times with 200 µl of 100 mmol/l NaCl. 100 µl of a preparation of the iodine-125-labeled 20B2-1B12 antibody whose activity has been brought to 250,000 cpm/100 µl by dilution in the TBS2 buffer are then incubated for 1 hour at 37° C. After five washes with a solution of 100 mmol/l NaCl, the radioactivity is measured, as described hereinbefore.

In both determinations, it is observed that the hemolymph of a severely parasitized oyster allows a signal of 20,000 cpm to be obtained, while the hemolymph of an oyster free from *Bonamia ostreae* allows a signal of 135 cpm to be obtained.

4. Direct determination on nitrocellulose with an antibody labeled using an enzyme For this determination, the antibody is used coupled to an enzyme. The coupling is carried out by activating alkaline phosphatase, marketed under the reference 567 752 by the company BOEHRINGER, with succinidinyl 4-(p-maleimidophenyl)butyrate marketed under the reference 22315 by the company PIERCE (USA), and by activating the antibody with (S-acetyl) mercaptosuccinic anhydride marketed under the reference 19 732-7 by the company FLUKA (FRG).

A nitrocellulose filter of 6 mm diameter is introduced into each of the wells of a microtitration plate. 25 µl of hemolymph from an oyster are deposit ed on each filter. After an incubation of 15 hours at 37° C., each filter is saturated with 200 µl of TBS1 buffer for 1 hour at 37° C. It is then washed three times with a solution of 100 mmol/l NaCl. 100 µl of a preparation of the 20B2-1B12 antibody label ed with alkaline phosphatase in solution, at a ratio of 1 µg per ml, in the TBS2 buffer are added. After an incubation of 1 hour at 37° C., the filter is washed five times with a solution of 100 mmol/l NaCl. Then 100 µl of a solution of paranitrophenyl phosphate at 1 mg per ml in a buffer of 100 mmol/l diethanolamine (pH 9.8 ) are added. After an incubation of 30 minutes at 20° C., 50 µl of a solution of 1 mol/l NaOH are finally added to each well. The color reaction is measured at 405 nm using a plate-reading spectrophotometer after removal of the nitrocellulose filters.

Under these conditions, measured at 405 nm, an optical density of 1.6 is obtained from a hemolymph of a moderately parasitized oyster, and of 0.16 from a hemolymph of an oyster free from *Bonamia ostreae*.

In place of the paranitrophenyl phosphate it is possible to use a precipitating substrate such as 5-bromo-4-chloro-3-indolyl phosphate marketed under the reference B 8503 by the company SIGMA (USA). Under these conditions, a deep blue coloration is obtained with hemolymph from parasitized oyster.

We claim:

1. A process for the immunological detection of the intracellular forms of a protozoan belonging to the specie *Bonamia ostrese* parasitizing the blood of a mollusk, which comprises taking a sample of the hemolymph of a mollusk infested by said protozoan and detecting the presence of the protozoan by contacting said sample with monoclonal antibodies which specifically recognize said protozoan and detecting any immunological complexes thereby formed wherein the preparation of the monoclonal antibodies comprises the steps of:

1) extracting said protozoan from the hemolymph of an infested mollusk, which extraction comprises the steps of:

removing any organ having a fibrous nature;
   crushing the mollusk devoid of said organ in the presence of a homogenization liquid, to produce an homogenized crushed mixture having particulate elements therein;

clarifying the homogenized crushed mixture by filtration to produce a filtrate containing said particulate elements and concentrating the particulate elements by centrifugation;

removing the particulate elements other than the protozoan sought by several differential centrifugations, thereby recovering said protozoan;

preparing a purified suspension of said recovered protozoan; and 2) using said purified suspension to prepare monoclonal antibodies which specifically recognize said protozoan.

2. A process according to claim 1, wherein the immunological technique used allows the detection of intracellular forms of the protozoan and in addition allows its quantification.

3. A process according to claim 2, wherein the monoclonal antibody used is the antibody secreted by the hybridoma deposited at the ECACC under the reference 87042307.

4. A process according to claim 1, wherein the homogenization liquid is seawater whose osmotic pressure has been adjusted to 1,000 mosm and which has been filtered through a membrane whose porosity does not exceed 0.22 µm and to which there is added 0.5 to 2% (v/v) of a neutral surfactant.

5. A process according to claim 4, wherein the surfactant is polyoxyethylene sorbitan 80 monooleate.

6. A process according to claim 1, which comprises successively carrying out a centrifugation in sucrose without a gradient, a centrifugation in sucrose with a gradient, and a centrifugation with a gradient of a polydisperse silica colloid covered with polyvinylpyrrolidone.

7. A diagnostic kit for the detection of a protozoan belonging to the genus Bonamia parasitizing a mollusk, which comprises the monoclonal antibody secreted by the hybridoma deposited at the ECACC under the reference 87042307 in combination with a container or support for said monoclonal antibody.

8. A diagnostic kit according to claim 7 wherein the monoclonal antibody is immobilized by adsorption on an insoluble support.

9. A diagnostic kit according to claim 7 wherein the monoclonal antibody is coupled to a marker.

* * * * *